United States Patent [19]
Maeda

[11] Patent Number: 5,833,460
[45] Date of Patent: Nov. 10, 1998

[54] CONTROLLED FORCE CROWN AND BRIDGE REMOVER

[76] Inventor: Ronald A. Maeda, 9872 Chapman, Garden Grove, Calif. 92641-2781

[21] Appl. No.: 833,733

[22] Filed: Apr. 9, 1997

[51] Int. Cl.⁶ .................................................... A61C 3/14
[52] U.S. Cl. ............................................................ 433/159
[58] Field of Search ...................................... 433/159, 160

[56] References Cited

U.S. PATENT DOCUMENTS

| Re. 29,889 | 1/1979 | Klein | 433/159 |
|---|---|---|---|
| 625,401 | 5/1899 | Lanterman | 433/159 |
| 1,628,499 | 5/1927 | Joesch | 433/160 |
| 3,377,705 | 4/1968 | Tofflemire | 433/155 |
| 3,834,026 | 9/1974 | Klein | 433/159 |
| 3,898,738 | 8/1975 | Linder | 433/159 |
| 4,609,353 | 9/1986 | Kline | 433/159 |
| 5,015,185 | 5/1991 | Cane' et al. | 433/159 |
| 5,044,954 | 9/1991 | Lukase et al. | 433/159 |
| 5,197,877 | 3/1993 | Andrew | 433/153 |

*Primary Examiner*—John J. Wilson
*Attorney, Agent, or Firm*—Anthony J. Coco

[57] ABSTRACT

A dental implement has two moderately flexible hemostat-like handles enabling an operator to apply safely controlled force through finger and thumb grips to bring coplanar bracing and grasping beaks toward one another for gentle removal of crowns or bridges from the mouth of a patient. The bracing beak bearing on the occlusal surface of an underlying tooth is readily modifiable in length or angular position to accommodate a variety of tooth sizes, locations and orientations, and the grasping beak is hollow ground to provide enhanced purchase on a gingival margin or supra-marginal notch of a crown. A method of crown or bridge removal utilizing an improved, lightweight, controlled force dental implement employs an iterative sectioning of the crown or bridge during removal.

11 Claims, 3 Drawing Sheets

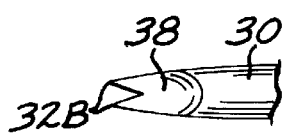
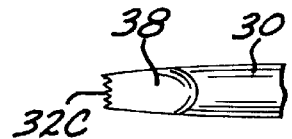
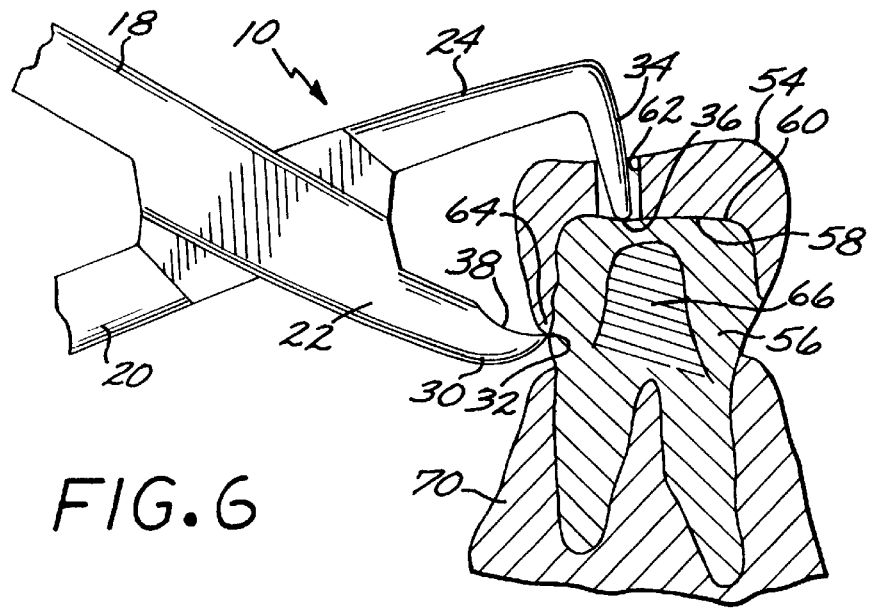
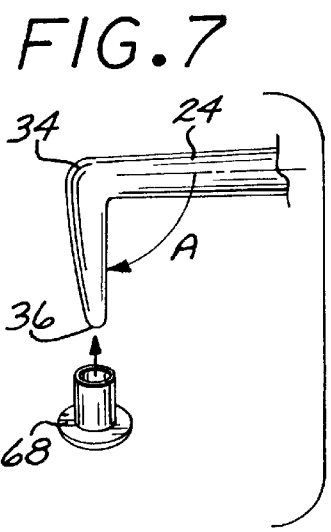
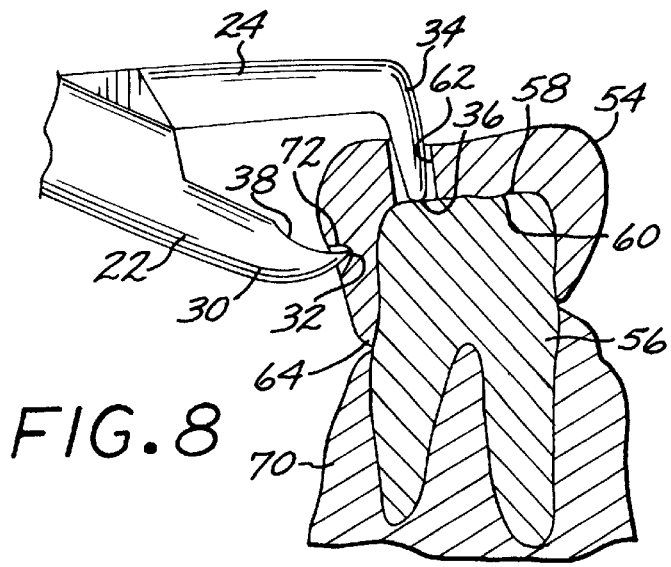

CONTROLLED FORCE CROWN AND BRIDGE REMOVER

BACKGROUND

1. Field of the Invention

This invention relates generally to hand-powered dental instruments. More particularly, the invention is directed to a method and hemostat-like implement for facilitating the removal of dental crowns or bridgework from teeth wherein the implement provides improved tactile sense and control of force as well as adjustability to accommodate various tooth sizes, locations and orientations.

2. Traditional Devices

In the practice of dentistry, artificial crowns are applied to protect a damaged tooth, and prostheses commonly known as bridges are emplaced to support teeth adjacent to a lost or extracted tooth. It is often necessary to remove such dental crowns or bridges, for example, to repair newly formed cavities in the covered tooth, or in the process of fitting and final elimination of temporary crowns and bridges. Reference henceforth to crowns will be understood to apply in general to bridges as well.

Traditionally, crowns have been removed by subjecting the dental patient to a variety of instruments including mallet and chisel, gear pullers, wire and rollers, and hook and sliding hammers. These and other instruments exert substantial forces which may tend to cause fracturing of the natural tooth. Additionally, many such instruments are difficult and time consuming to place, and thus much more likely to be used aggressively, increasing the likelihood of risk to the tooth. In contrast, an instrument that is quickly and easily placed and withdrawn encourages more deliberate and patient assessment of the crown removal process.

U.S. Pat. No. 5,197,887—Andrew, discloses a complex multiple hook and wire arrangement for lifting a crown toward a fixed platform remote from and above the tooth. U.S. Pat. No. 3,834,026—Klein, discloses crown removing pliers having jaws that grip the vertical surfaces of a crown in a process similar to that of the tooth extraction process. U.S. Pat. No. 4,609,353—Kline, discloses pliers having a sleeve and rotatable pin member on a distal jaw opposing a tapered member for engaging the lower margin of a crown and having proximal handles whereon palm pressure is applied to bring the distal jaws toward one another. In the preferred use of the Kline invention, the pin member is inserted in one of four occlusal holes at a radial distances from the pulpal center of the tooth, near points for which the dentin structure over the pulp is marginally thinner and therefore less protective than that at the center of the occlusal surface. Also, the pin member and the opposing tapered member are not advantageously coplanar, thus allowing the potential to exist a torquing moment of the crown workpiece, about an axis perpendicular to the longitudinal axis of the tooth. Further, the pin sleeve may result in blockage of an operator's vision of the tip of the pin, and the angle of the pin itself is believed to be non-adjustable. Finally, the pliers-like configuration of the relatively massive stainless steel handle requires application of the operator's palm, reducing tactile feel in comparison to hemostat-like application of finger-thumb pressure, and jeopardizing the safety of the tooth structure through potentially excessive force.

None of the prior art devices fulfills the long felt need for a lightweight, simply constructed and easily adjustable crown and bridge removal tool that imparts a high tactile sense and provides improved control of force to minimize procedure time, patient discomfort and tooth damage during the crown removal process.

It is therefore an object of this invention to provide a dental hand-held tool for more quickly and easily removing a crown or bridge with reduced discomfort for the patient and minimal damage to the crown, bridge or tooth.

It is another object of the invention to provide a lightweight scissors-like to hemostat-like crown removal implement with a bracing beak and a margin-engaging grasping beak operating in coplanar mutual opposition to establish a firm and stable grip on the crown during removal and subsequent transit from the mouth of the patient.

It is yet another object to provide a crown removal tool which is simple to use and comfortably controllable to reduce the potential for exertion of excessive force by a practitioner.

It is a further object to provide a dental instrument having a bracing beak that can be readily modified in length or angular position to safety adapt the tool for a variety of tooth sizes, locations and orientations.

It is another object to provide an improved crown removal method utilizing a lightweight, controlled force, adjustable hand-held dental tool and employing an iterative sectioning of the crown as required.

SUMMARY OF THE INVENTION

The present invention is directed to apparatus and method for removing dental crowns and bridges, the apparatus including a hand-held implement that is scissors-like or hemostat-like in that it is configured to be operated by the thumb and fingers of a dental practitioner or operator, as contrasted with pliers-like implements requiring pressure from the palm of the operator. The apparatus features two moderately flexible handles for pivotally propelling opposing coplanar beaks, a bracing one of which is angularly and lengthwise adjustable to bear on the surface of a tooth, and a grasping one of which is modifiable to provide improved purchase on a variety of crown margins or surfaces.

BRIEF DESCRIPTION OF THE DRAWINGS

FIG. 5B is an alternate partial plan view taken along line 5—5 of FIG. 3 illustrating a notched grasping beak element thereof;

FIG. 5C is an alternate partial plan view taken along line 5—5 of FIG. 3 illustrating a serrated grasping beak element thereof;

FIG. 6 is a partial side view of the implement of FIG. 1 and a tooth in section illustrating a typical initial margin grasping position of the implement;

FIG. 7 is an exploded partial side view of the bracing beak element of FIG. 1 illustrating a pressure dispersing cap element;

FIG. 8 is a partial side view of the element of FIG. 1 and a tooth in section illustrating a typical initial notch grasping position of the implement

DETAILED DESCRIPTION OF EXEMPLARY EMBODIMENTS

When the seal of a dental crown is defective, or a crown or bridge must be removed for repair, adjustment or replacement, it is important that the neither the crown or bridge nor the underlying tooth be damaged during the process of removal. Implements for this purpose that transmit excessive force or impact torquing motion to the site of the tooth are less than satisfactory, as are implements which scratch or chip the surface of the crown, or are difficult to adapt to varying tooth conditions. An implement which self-limits the transmittable force, greatly reduces the possibility of torquing, and is both gentle to the crown surface and easily adjustable for a variety of crown sizes and angles would help considerably to effect a safe, professional and rapid removal of a crown or bridge.

Figure 1:
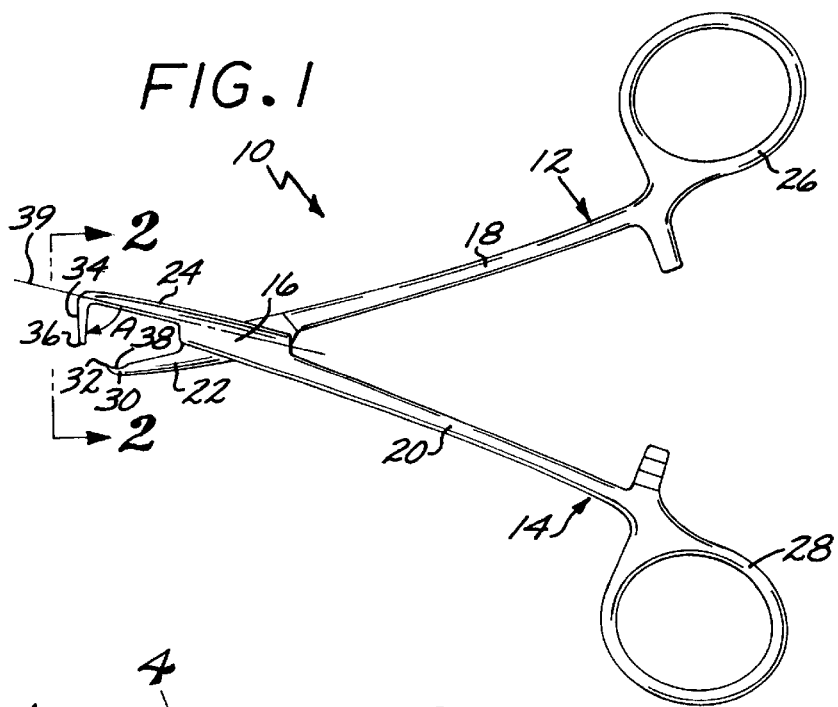
FIG. 1 is a side view of a crown and bridge remover implement illustrating an unslotted bracing beak embodiment of the present invention.

With reference to FIG. 1, a non-slotted crown and bridge removing implement 10 is shown in an open position preparatory to being applied to a crown and tooth (shown in more detail in FIGS. 6 and 8). The implement 10 has first and second hemostat-like arms 12,14 pivotally joined at a pivot area 16 by any suitable pivot pin (not shown), defining first and second handle portions 18 and 20 on the proximal side of the pivot area 16, and respective first and second jaw portions 22 and 24 on the distal side of the pivot area.

The first and second handle portions 18,20 are selected to be of sufficiently small size and moderate flexibility to self-limit any applied forces by bending in the event that excessive force is used. A suitable material for the purpose would be similar to that used in the Mosquito 5" hemostat manufactured by Hu-Friedy and supplied by Henry Schein of Port Washington, N.Y.

A thumb grip 26 and a finger grip 28 are disposed on the free ends of respective handle portions 18 and 20. The thumb and finger grips 26,28 may be covered with a plastic or rubber material, and may be reconfigured and bent out of the plane of arms 12,14 as will be described below, for enhanced operator comfort and control.

Figure 2:
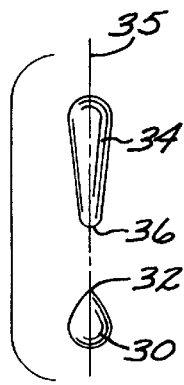
FIG. 2 is an end view taken along line 2—2 of FIG. 1 illustrating the planar alignment of bracing and grasping beak elements thereof.

A grasping beak 30 having a crown-engaging edge 32 is formed on the end of the first jaw 22, and an adjustable bracing beak 34 having an occlusal-bearing tip 36 is formed on the end of the second jaw 24. Grasping beak 30 and engaging edge 32 are aligned with the non-slotted bracing beak 34 and bearing tip 36 to operate in mutual opposition within the operating plane formed by first and second handle portions 18 and 20, as more clearly seen in FIG. 2, taken along line 2—2 in FIG. 1. Line 35 in FIG. 2 represents an end view of the operating plane just described.

Returning to FIG. 1, the bracing beak 34 forms a bend angle A with the longitudinal axis 39 of the second jaw portion 24, This angle A may be modified within the plane represented by plane trace line 35 as will be described below to accommodate varying tooth sizes and locations.

The first jaw 22 and grasping beak 30, except for variations in the engaging edge 32, remain essentially the same for the various embodiments of the present invention and will bear the same reference numerals. In contrast, the second jaw and adjustable bracing beak, having a significantly different configuration in another embodiment (see, e.g., FIGS. 3 and 4), are given different reference numerals to distinguish them from the corresponding elements in FIG. 1. However, in all embodiments, it is essential to note the adjustable bracing beak and the grasping beak are aligned to operate in the plane formed by the first and second handle portions 18,20 and represented by plane trace 35 in FIG. 2. This greatly minimizes the potential for applying a disadvantageous torque to the tooth and crown, a potential that would exist in an implement wherein mutually opposing elements are non-coplanar.

Figure 3:
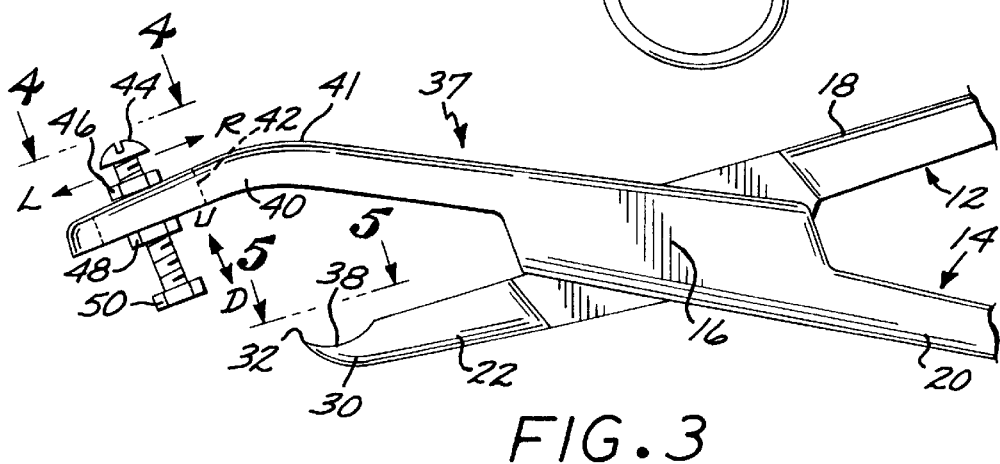
FIG. 3 is a partial side view of a crown and bridge remover implement illustrating a slot and bolt bracing beak embodiment of the present invention.
Figure 5A:
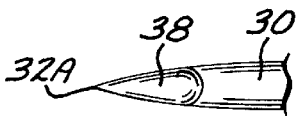
FIG. 5A is a partial plan view taken along line 5—5 of FIG. 3 illustrating a single-pointed grasping beak element thereof.

A slot and bolt embodiment 37 of the present invention is illustrated in FIG. 3. The grasping beak 30 and engaging edge 32 are essentially identical to the grasping beak and engaging edge of FIG. 1. In either embodiment, edge 32 is tapered and grasping beak 30 is preferably hollow ground with recessed portion 38 (FIGS. 1, 3, and 5A–5C) for improved grip on the gingival margin or filed purchase area of the crown as will be described below. It will be noted that a hollow grinding of the grasping beak 30 directs a grasping force in the direction of removal, i.e., toward lifting the crown from the tooth, whereas a grasping beak that is merely tapered would direct the force disadvantageously at an angle toward the tooth. FIGS. 5A through 5C illustrate a range of modifications to the grasping edge available to the dental practitioner according to preference. FIG. 5A shows a thin and single-pointed grasping edge 32A for interproximal access; FIG. 5B shows a grasping edge 32B which has been notched to provide two to three points of purchase; and FIG. 5C shows a serrated grasping edge 32C for a wider grip on the crown.

Figure 4:
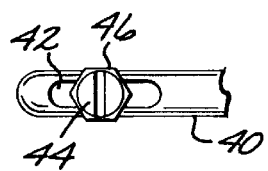
FIG. 4 is a partial plan view taken along line 4—4 of FIG. 3 illustrating the slot and bolt elements thereof.

Returning now to FIG. 3, a slotted bracing beak 40 is formed with a longitudinal slot 42, shown in plan view in FIG. 4. Slot 42 perpendicularly receives a threaded bolt 44 having upper and lower lockdown nuts 46 and 48, one on each side of the slot 42. A bracing means such as a bearing nut 50 for dispersing axial pressure on the tooth may also be threaded onto blot 44. The distal tip 52 of threaded bolt 42 is adapted to bear, in a manner similar to that of bearing tip 36 (FIG. 1), on the occlusal surface of an underlying tooth (FIGS. 6 and 8), or on a base or coping in the case of a telescoping crown (not shown).

A typical initial position of the crown removing implement 10 is illustrated in FIG. 6. The description which follows of the position and basic operation of the non-slotted embodiment 10 is generally applicable as well to that of the slotted embodiment 37. A crown 54 or bridge is in place atop an underlying tooth 56, with the lower surface 58 of the crown in contact with the occlusal dentin surface 60 of the tooth. A virtually identical configuration results if a telescoping crown (not shown) is involved, the crown then being in contact with a base or coping (not shown) instead of the tooth dentin 60. An access hole 62 is predrilled through the occlusal surface of the crown 54 so that the tooth surface 60 is exposed.

The bearing tip 36 of the bracing beak 34 is shown impinging on the tooth dentin surface 60, while the engaging tip 32 of grasping beak 30 is shown engaging a gingival margin 64 of the crown 56. If much of the central tooth structure is lost so that very little dentin covers the tooth central pulp 66, a bracing means for dispersing pressure in the form of a flared cap 68 (FIG. 7) may be pressed onto the bearing tip 36 so that the tip 36 will not breakthrough the dentin 60 and injure the pulp 66.

In a similar manner, for the slot and bolt embodiment 37 (FIG. 3), the distal tip 52 of threaded bolt 44, instead of the bearing tip 36, bears on tooth surface 60. Bearing nut 50 is employed with slotted implement 37 to disperse pressure on the tooth analogously to the flared cap 68 with non-slotted implement 10.

For either embodiment 10 or 37, the gingival margin 64 of the crown 54 may be top close to the gum tissue 70 of the patient, or too smooth to permit grasping by engaging tip 32. In FIG. 8, a small notch 72 has been ground into a buccal or lingual surface of the crown 54 at a point slightly above the gingival margin 64. The engagement edge 32 of grasping beak 30 is shown engaging the supramarginal notch 27 so that upward pressure may be exerted on the crown 54. As in FIG. 6 where the engagement edge 32 is grasping the gingival margin 64, the hollow ground recess 38 provides a holding configuration which directs the force toward the direction of removal of the crown 54, not toward the tooth 56 as would a tapered but not hollow ground beak.

Figure 9:
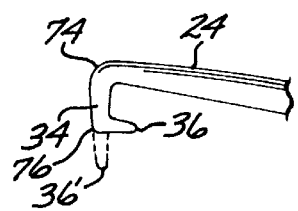
FIG. 9 is a partial side view of the bracing beak element of FIG. 1 illustrating a length modified bearing tip position in ghost lines.
Figure 10:
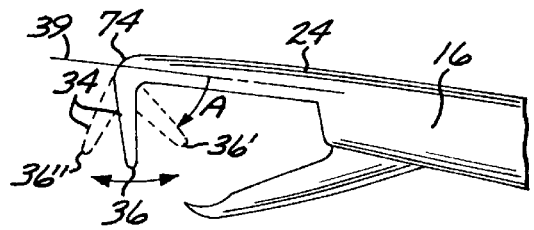
FIG. 10 is a side view of the implement of FIG. 1 illustrating angle modified bearing tip positions in ghost lines.

In operation, the length and angle of the bracing beak 34 are modified as illustrated in FIGS. 9 and 10 by heating the distal end of the second jaw portion 24 until the length metal of the jaw portion 24 is bendable, utilizing for example an ordinary dental office Bunsen burner (not shown). The operator will modify the bracing beak's length and angle according to the operator's professional judgment of the optimum relationship between the location of the crown access hole 62 and the crown margin 64 or the crown notch 72 (FIGS. 6 and 8).

Returning to FIG. 9, the length of the bracing beak 34 is changed by bending the second jaw 24 at a new bend point 74. The bracing beak 34 is then straightened to eliminate the former bend point 76, resulting in a lengthened bracing beak 34, with the pre-modified bearing point 36 now relocated to the modified bearing point location 36' (shown in ghost lines).

Turning to FIG. 10, the angle A, formed by the juncture of the bracing beak 34 with the longitudinal axis 39 of second jaw portion 24, is modified following the same heating procedure as above, by bending the bracing beak 34 about the bend point 74 as shown in FIG. 10. The bearing tip 36 is shown relocated back toward the pivot area 16 or forward away from the pivot area 16 by ghost lines at 36' and 36" respectively. Bend angle A may be adjusted within the operating plane represented by end view trace 35 (FIG. 2) on either side of the right angle of −90° through the range of approximately −70° to −110°.

Figure 11:
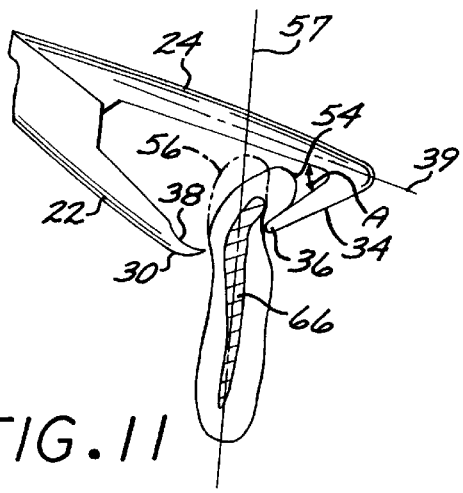
FIG. 11 is a partial side view of the implement of FIG. 1 and a tooth in section illustrating adaptation of the implement to a crown which corrects a former (ghost lines) tooth misalignment.

A typical example of an angularly modified bracing beak 34 is illustrated in FIG. 11, wherein an anterior tooth 56 having longitudinal root axis 57 is misaligned with adjacent teeth (not shown) and has been fitted with a crown 54 in proper alignment with such teeth but necessarily at an angle to root axis 57. The angle A of the bracing beak 34 has been reduced to reach lingual of the crown 54 to bear on the underlying tooth 56, reducing the potential for tooth fracture during the crown removal process.

To describe a method for removing a crown or bridge utilizing either the non-slotted implement 10 or the slotted implement 37, reference is again made to FIG. 6.

A crown access hole 62 is made in the crown 54 and through the crown lower surface 60 to accommodate the bracing beak 34. The operator modifies the length, taper, bearing tip diameter and angle of the bracing beak 34 as described above to compensate for individual tooth characteristics known in the art including tooth and crown shape, size, angle and location; the thickness of protective dentin; and retentive features such as axial, occlusal or incisal grooves, undercuts in the preparation of the tooth or crown, and bonding of the crown to the tooth.

Depending on the relative size of the underlying tooth 56, the operator may grind the bracing beak 34 to provide a greater or lesser taper to the beak. Shortening the tapered bracing beak 34 develops a wider bearing tip 36 suitable for larger underlying teeth; maintaining a longer, and therefore thinner, tapered beak facilitates access to smaller, more pointed teeth. As previously described, a wider bearing surface for bearing tip 36 may also be attained by fitting a pressure dispersing cap 68 at the end of the tip 68 as shown in FIG. 7.

The bracing beak 34 is then placed in the hole 62 until the modified bearing tip 36 rests on the occlusal 60 of the underlying tooth 56.

Modification of the slotted bracing beak 40 for utilization of the slotted implement 37 follows a similar pattern. Referring to FIGS. 3 and 4, the distal end of the second arm [20] 14 is heated and bent at point 41 to an angle estimated by the operator to approximate a predetermined position for the operation of the threaded bolt 44. Bolt 44 is then inserted perpendicularly into bracing beak slot 42, and slid longitudinally along the slot 42 in the left and right directions indicated by arrows L and R, respectively, to an initial trial position. The bolt 44 is secured in place by upper and lower lockdown nuts 46 and 48, respectively.

The distal tip 52 of bracing beak bolt 44 is then emplaced within the crown access hole 62 and the interrelationship of the bracing beak 40 with the grasping beak 30 is observed. If further adjustment is required, the operator changes the angle of bracing beak 40 by heating, the position of threaded bolt 44 by sliding it along the slot 42, or the effective length of the bolt 44 up or down, as indicated by the U and D arrows in FIG. 3, by adjusting the lockdown nuts 46 and 48 until an optimum positioning of the beaks 30, 42 is achieved. Bearing nut 52 may be threaded flush with the distal tip 52 to increase the bearing surface for dispersing pressure on the tooth analogously to the function of pressure dispersing cap 68 (FIG. 7). The following discussion of the operation of the non-slotted implement 30 applies equal to the slotted implement 37.

Turning again to FIG. 6, the sharp engaging edge 32 of grasping beak 30 then engages the gingival margin 64 of the crown 54. If the margin 64 is difficult to engage, the operator may cut a shallow notch 72 slightly above the margin 64 to receive the engaging edge 32 as shown in FIG. 8.

The handle portions 18, 20 are squeezed together using thumb and finger grips 26 and 28 (FIG. 1), respectively, applying only moderate pressure and taking care to avoid rocking or prying forces that could cause the tooth 56 to fracture at the point of engagement 64 or 72. The thin arms 12, 14 help to prevent the application of excessive force during the attempt to remove the crown.

An important aspect of implementing the concept of controlled force involves the principle that when a crown does not release with moderate force, the crown should be divided and each section worded separately, dividing the sections again as necessary.

Figure 12:
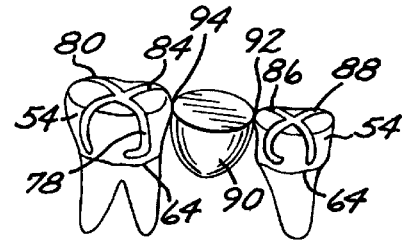
FIG. 12 is a perspective view illustrating a pattern of grooves cut in a bridgework according to a method of the present invention.

The thicker the crown 54 is, the more difficult it will be to remove, and the underlying tooth 56 is often weak. Since more material can be added to a new crown, but new tooth structure cannot be added if the tooth 56 fractures because of excessive linear force or torque, the crown may be divided into smaller sections so that less force is required on each section. FIG. 12 illustrates a pattern of grooves used to divide the crown 54.

After a first attempt to remove the crown 54 with moderate pressure, a groove 78 may be cut in the crown from the occlusal to the buccal, or a groove 80 from the occlusal to the labial, each just short of the gingival margin 64 of the crown, and another attempt may be made. It is desirable to avoid cutting through the margin 64 if possible, since the crown 54 may be used as a temporary or provisional crown by filling in the defects with acrylic. However, if the crown does not yield, the groove must be cut through the margin 64, or additional grooves 82 through 88 cut in the crown, and the implement 10 or 37 tried again. For particularly difficult bridge removals, it may be necessary to sever the pontic 90 from the anchoring crowns by cutting through the pontic at abutment areas 92 or 94.

Figure 14:
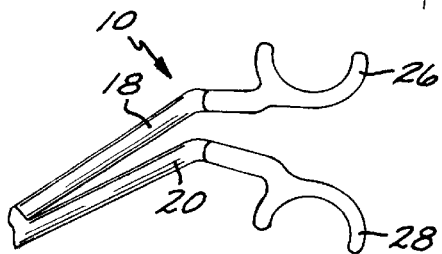
FIG. 14 is a side view of the implement of FIG. 1 illustrating a modified closure condition of the thumb and finger grip elements thereof.
Figure 13:
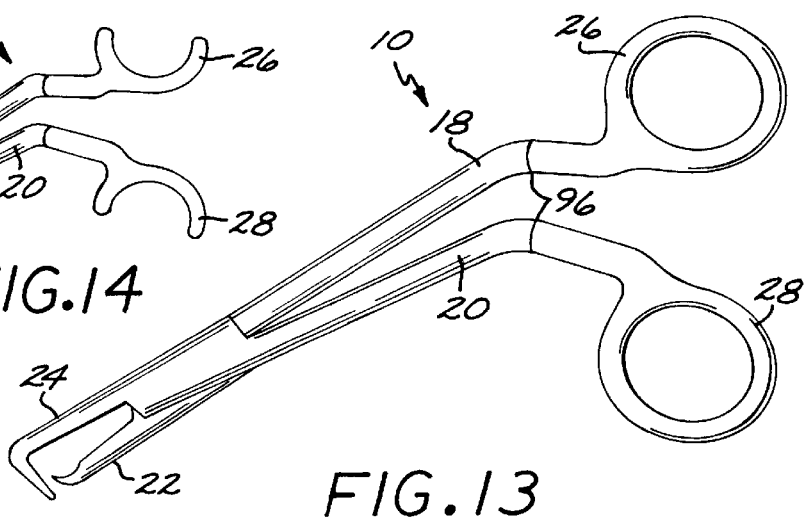
FIG. 13 is a side view of the implement of FIG. 1 illustrating a modified angle of the thumb and finger grip elements thereof.

To further advance the goal of controlled force removal for crowns, a variety of modifications may be made to the thumb grip 26 and finger grip 28 of either implement 10, 37 for greater operator comfort and control. FIG. 13 illustrates an implement 10 whose thumb and finger grips 26, 28 have been heated and bent at some angle determined by the operator to aid in reaching a difficult area of the mouth. Independently of any change in angles, one or both grips may be custom fitted with self curing acrylic or elastomeric material for cushioning fingers, as indicated by the cushioning boundaries 96. The thumb and finger grips 26, 28 may also be bent out of the operating plane as it has been defined above, or opened as represented in FIG. 14 to accommodate various sizes and shapes of an operator's hand.

With the benefit of the preceding detailed description and disclosure of the general principles of the present invention, changes that do not depart from those principles will be apparent to those skilled in the art. Therefore, the scope of the present invention is limited only by the following claims.

I claim:

1. An implement for removing, from teeth in the mouth, a dental crown or bridge, said implement comprising:

first and second arms pivotally joined for rotation relative to each other, the arms having first and second moderately flexible handle portions defining their respective proximal ends, and first and second jaw portions defining their respective distal ends, such that the jaw portions are propelled toward one another when the handle portions are manipulated toward one another in a hemostat-like manner by the fingers and thumb of a dental practitioner;

a thumb grip formed on the first handle portion and a finger grip formed on the second handle portion;

a hollow ground grasping beak formed on the first jaw portion, the grasping beak having a sharp edge adapted to engage a gingival margin or vertical surface of said crown; and an adjustable bracing beak formed on the second jaw portion, the bracing beak having a tip adapted to bear on a tooth through a preformed hole in the crown, within an arc generally coplanar with the plane of motion of said grasping beak, said bracing beak comprising an integral projection of the second jaw portion bent toward the first jaw portion at a modifiable bend angle to the longitudinal axis of said second jaw portion, said bracing beak bearing tip being tapered to diverge toward said second jaw portion, thus providing a self-limiting stop to prevent excessive intrusion of the tip into the preformed hole in the crown.

2. The implement of claim 1 wherein the bend angle of said bracing beak tip is preferably within the range of −70° to −110° with respect to the second jaw portion longitudinal axis.

3. The implement of claim 1 wherein said bracing beak tip is fitted with a bracing means for dispersing axial pressure on the tooth within the preformed hole of the crown.

4. The implement of claim 1 wherein the bracing beak comprises an integral projection of said second jaw portion, said projection being bent at an obtuse angle toward the first jaw portion and having a slot formed therethrough within the central plane defined by said first and second arms, said slot receiving a threaded bolt perpendicular thereto, said bolt having at least one lockdown nut disposed on each side of the slot to secure longitudinal and perpendicular travel of the bolt within the slot preparatory to a distal bearing tip of the bolt being emplaced into said preformed hole of the crown.

5. The implement of claim 4 wherein said bolt bearing tip is fitted with a bracing means for dispersing axial pressure on the tooth within the preformed hole of the crown.

6. A method for removing, from a tooth in the mouth, a dental crown having at least occlusal, lingual, and buccal or labial surfaces and gingival margins, said crown contacting an underlying occlusal surface of the tooth or a base thereon, said method comprising the steps of:

providing a hemostat-like implement having first and second moderately flexible arms, an adjustable bracing beak including a bearing tip disposed on a distal end of the second arm, a crown grasping beak having a hollow ground edge disposed on a distal end of the first arm and adapted to operate within an arc coplanar with the plane of motion of the bracing beak, and thumb and finger grips on proximal ends of the first and second arms, respectively;

drilling a hole through an occlusal surface of the crown to access the surface of the underlying tooth or base thereon;

adjusting the bracing beak lengthwise and angularly within said coplanar arc to advantageously accommodate tooth size, location and orientation with respect to the grasping beak;

emplacing the bracing beak within the crown access hole so that the bearing tip bears on the underlying tooth or base and the grasping beak engages the crown;

employing the thumb and finger grips to bring the grasping beak and bracing beak gently toward one another, thereby exerting simultaneously a bracing force on the occlusal and an opposing grasping force on the crown, the simultaneous forces being advantageously limited by the moderate flexibility of the first and second arms;

cutting a groove in the crown if necessary from the occlusal outwardly to the buccal or labial surface thereof, just short of the gingival margin; and repeating the step of bringing the grasping and bracing beaks toward one another until the crown is removed.

7. The method of claim 6 wherein the step of adjusting the bracing beak further comprises:

grinding the distal end of the second jaw portion until a predetermined taper is achieved; and heating and bending the bracing beak toward the first jaw portion to achieve a predetermined length and angle of the bearing tip.

8. The method of claim 6 wherein the step of adjusting the bracing beak further comprises:

providing a slot through the second arm adjacent the distal and thereof within the central plane defined by the first and second arms; providing a threaded bolt having at least one lockdown nut disposed on each side of said slot;

temporarily installing the threaded bolt perpendicularly within the slot and securing the nuts so that a distal end of the bolt faces toward the grasping beak;

withdrawing the bolt and heating the slotted portion of the bracing beak thus established;

bending said slotted portion to achieve an approximate predetermined angle for the final position of the threaded bolt;

reinstalling the bolt and securing the nuts on each side of the slot; and repeating the withdrawing, heating and reinstalling steps as necessary until the final predetermined position of the threaded bolt is achieved.

9. The method of claim 8 wherein the steps of reinstalling the bolt and emplacing the bracing beak further comprise:

providing a bearing nut having a largest outer diameter smaller than the diameter of said crown access hole, said bearing nut disposed at the distal end of the threaded bolt so that said bearing nut outer surface is flush with the distal end of said bolt; and emplacing the bracing beak in the crown access hole so that the bearing nut impinges on the occlusal surface of the underlying tooth or base, thereby dispersing said bracing force and relieving pressure on the tooth.

10. The method of claim 6 wherein the step of emplacing the bracing and grasping beaks further comprises positioning the grasping beak so that the hollow ground edge thereof engages the gingival margin of the crown.

11. The method of claim 6 wherein the step of emplacing the bracing and grasping beaks further comprises:

cutting an engagement notch in a buccal or lingual surface of the crown; and positioning the grasping beak so that the hollow ground edge thereof engages the engagement notch.

* * * * *

UNITED STATES PATENT AND TRADEMARK OFFICE
CERTIFICATE OF CORRECTION

PATENT NO : 5,833,460
DATED : Nov. 10, 1998
INVENTOR(S) : Ronald A. Maeda

It is certified that error appears in the above-identified patent and that said Letters Patent is hereby corrected as shown below:

Column 1, line 53: insert --for-- between "exist" and "a".
Column 2, line 8: delete "to" and insert --or-- therefor.
Column 2, line 19: delete "safety" and insert --safely-- therefor.
Column 3, line 1: delete "element" and insert --implement-- therefor.

Column 5, line 13: delete "breakthrough" and insert --break through--.
Column 5, line 22: delete "top" and insert --too-- therefor.
Column 5, line 27: delete "27" and insert --72-- therefor.
Column 5, line 36: delete "length" and insert --light-- therefor.

Column 6, line 34: delete "[20]".

Column 7, line 6: delete "worded" and insert --worked-- therefor.

Signed and Sealed this

Twentieth Day of April, 1999

Attest:

Q. TODD DICKINSON

*Attesting Officer*   *Acting Commissioner of Patents and Trademarks*